United States Patent [19]
Miller

[11] Patent Number: 5,051,092
[45] Date of Patent: Sep. 24, 1991

[54] DENTAL ANCHOR AND A DRILL FOR USE THEREWITH

[75] Inventor: Alan N. Miller, New City, N.Y.

[73] Assignee: Coltene/Whaledent, Inc., New York, N.Y.

[21] Appl. No.: 303,900

[22] Filed: Jan. 30, 1989

[51] Int. Cl.⁵ .............................................. A61C 5/04
[52] U.S. Cl. ..................................... 433/225; 433/165
[58] Field of Search ............... 433/220, 221, 225, 165, 433/75

[56] References Cited

U.S. PATENT DOCUMENTS

| | | | |
|---|---|---|---|
| 1,200,921 | 10/1916 | Chester | 433/165 |
| 2,453,696 | 11/1948 | Brooks | 433/165 |
| 4,449,937 | 5/1984 | Weissman | 433/225 |
| 4,480,998 | 11/1984 | Carse | 433/225 |
| 4,571,187 | 10/1984 | Weissman | 433/221 |
| 4,579,532 | 4/1986 | Lustig | 433/225 |
| 4,616,999 | 10/1986 | Weissman | 433/225 |
| 4,767,332 | 8/1988 | Weissman | 433/225 |
| 4,820,159 | 4/1989 | Weissman | 433/225 |

FOREIGN PATENT DOCUMENTS

| | | | |
|---|---|---|---|
| 76084 | 4/1983 | European Pat. Off. | 433/225 |
| 3543737 | 6/1987 | Fed. Rep. of Germany | 433/165 |

Primary Examiner—Cary E. O'Connor
Attorney, Agent, or Firm—Helfgott & Karas

[57] ABSTRACT

An anchoring pin for retention of a dental restoration onto a tooth stub, the pin including an upper retention portion on which a restoration is to be formed, a lower anchoring threaded portion self-threadable in a bore pre-drilled in the tooth stub and a stop collar interconnected between the retention portion and the anchoring portion. A stepped dental drill having two coaxial drill bits of different diameters is provided, which in addition to forming the bore makes a counterbore at the mount of the bore at the exposed excavated surface of the tooth. The counterbore receives the stop collar of the anchoring pin as the latter is driven into the tooth bore thereby preventing bottoming out of the pin so as to avoid concentrated stress at the tip of the pin and also providing distribution of stress as the wider collar abuts the bottom of the counterbore.

26 Claims, 2 Drawing Sheets

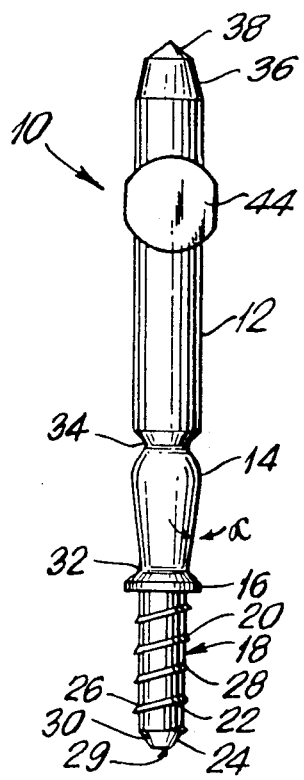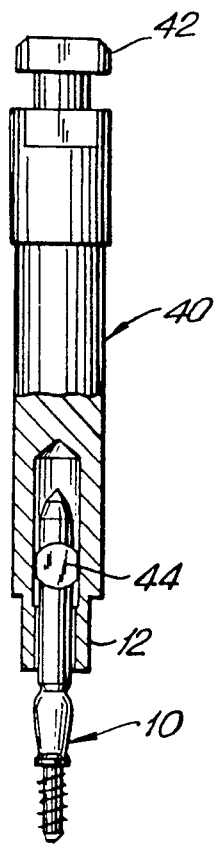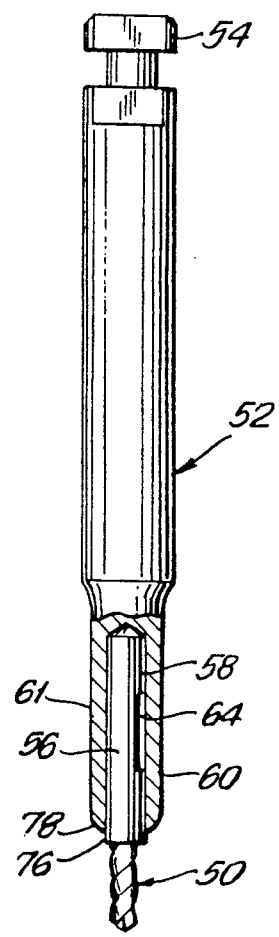
FIG. 1    FIG. 2    FIG. 3
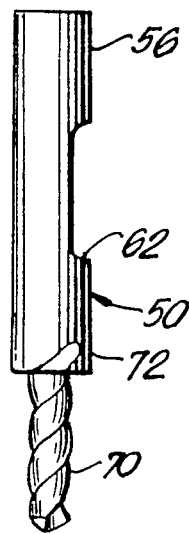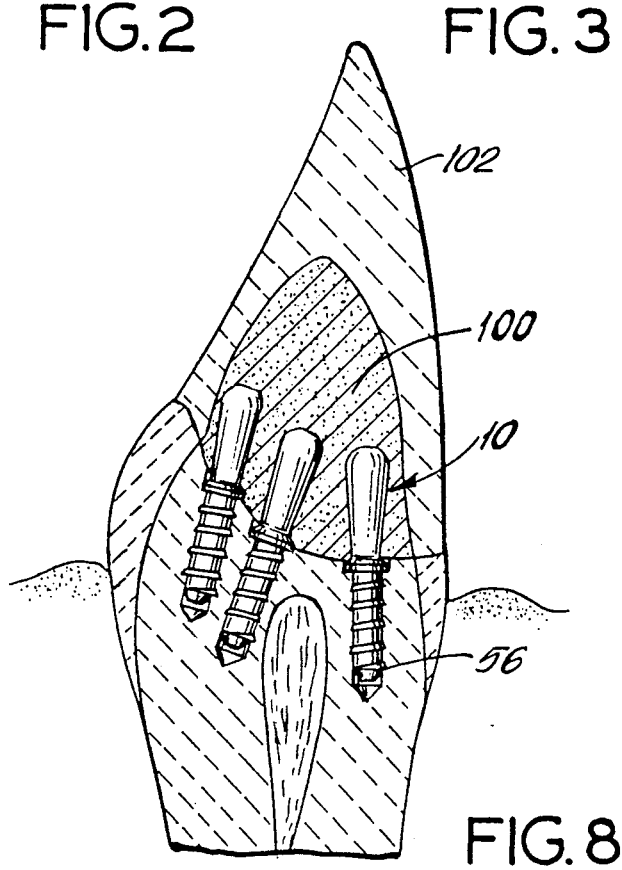
FIG. 4    FIG. 8

DENTAL ANCHOR AND A DRILL FOR USE THEREWITH

BACKGROUND OF THE INVENTION

The present invention relates to a dental anchor or pin for aiding in the retention of a dental restoration and, more particularly to a dental anchor provided with means for reducing stress both upon a tooth stub in which it is inserted as well as reducing cracks in the restoration which is built up over the anchor.

Dental anchors or pins for retaining dental restorations are well-known in the art of dentistry, particularly anchors or pins having threads thereon for securement in the tooth structure. The tooth stub is typically prepared by cutting it down and making a bore in the tooth stub, in which a dental post is inserted. Additional bores are formed in the tooth structure, into which pins or anchors are threaded. These pins have portions extended upwardly of the tooth surface for aiding in the retention of the dental restoration as well as avoiding rotation of the restoration on the tooth stub. Such anchoring pins are very small, i.e. in order of 0.03 inches in diameter and 0.2 inches in length. These pins are typically first loaded into a dental power tool or holder and inserted into prepared bores or channels made in the body of the tooth. Such bores or channels are formed in the body of the tooth by means of dental drills.

Anchors or pins for anchoring and supporting a dental restoration are typically comprised of two portions, one of which is an anchoring portion threaded in the bore formed in the body of the tooth and another is a retention portion for embedding into the restoration. Typically the retention portion is coupled to a manipulating head extending from the retention portion and connected by at least one reduced diameter portion. In this way when the pin is threaded into the bore formed in the tooth the pin severs automatically upon bottoming out the lower end of the bore. The anchoring portion remains in the tooth with the retention portion extending upwardly from the tooth surface.

Dental anchors or pins having a buttress-type thread has been disclosed in assignee's co-pending patent application Ser. No. 191,347. They have proven to have a most satisfactory retention capability inasmuch as buttress-type threads, particularly the reverse buttress-type threads described, provide improved holding power in the dentition and reduce the amount of dental damage during insertion.

The aforementioned co-pending application discloses a dental anchor having a buttress-type thread, where the buttress-type thread includes a substantially planar lower surface facing toward the insertion end of the dental anchor, a beveled upper surface which tapers inwardly towards the retention portion of the dental anchor, and a sharp crest portion disposed between the planar lower surface and angled upper surface. A top member or collar is provided between the anchoring portion and the retention portion. The stop member limits the depth of insertion of the dental anchor into the bore.

It should be appreciated, however, that even with highly efficient dental anchors or pins having buttress-type threads there is a continuous interest in further reducing or minimizing any stress on existing dentin, especially at the bottom or seat portion of the bore which receives the dental anchor.

Accordingly, while the use of dental anchors having a buttress-type threads thereon has been proven quite useful in the dental art, further improvements in such dental anchors and means for anchoring the same in the tooth body are still of importance in order to yet further reduce any stress on dentin material and to facilitate anchoring or such pins. It is also of interest to facilitate insertion at surfaces of teeth which are inclined, curved or have any other non-planar exposed surfaces.

SUMMARY OF THE INVENTION

It is an object of the present invention to provide a dental anchor which avoids the aforementioned problems of prior art dental anchors.

Another object of this invention is to provide a drill for making channels or bores receiving the dental anchors to substantially reduce stress on the dentin material of the tooth.

Yet another object of the present invention is to facilitate preparation of the tooth stub for building thereon a dental restoration.

It is a further object of the present invention to provide means for and a method of installing dental pins which would substantially minimize stress on the tooth stub as well as on the dental restoration to be built thereon.

Briefly, the objects of the present invention are attained by a dental anchor for the retention of a superstructure on a tooth stub and insertable into a bore formed in the tooth stub. The dental anchor comprises an upper retention portion, on which the superstructure or a dental restoration is to be formed, an anchoring portion having a threaded portion thereon and being self-threadable into the bore in the tooth stub to secure therein the dental anchor, and a stop provided between the retention portion and the anchoring portion for limiting the depth of insertion of the dental anchor into the channel. The retention portion is of a smooth continuous configuration having no sharp corners thereby substantially reducing stress on the superstructure, avoiding the occurrence of cracks therein and providing a smooth distribution of the restoration material over the retention portion.

In an embodiment, smoothly shaped undercuts are formed along the retention portion adjacent the anchoring portion. The restorative material is packed in these undercuts to provide improved retention onto the tooth stub.

The objects of the invention are also attained by a stepped dental drill which not only drills the anchor receiving bore in the tooth stub but also forms a counterbore at the exposed excavated surface of the tooth. The drill is matched to the anchor so that the bore will be longer than the threaded portions of the anchor. When the dental anchor engaged in a holder is rotatably inserted into the bore the stop collar seats into the counterbore to stop further insertion of the anchor and prevent bottoming out of the anchor. The collar also serves to distribute the stress over a flat wide surface rather than concentrating stress on the bore edges having the threading. By making the collar wider than the crest of the threads, the collar will have a chance to sit on supported dentition which also distributes and reduces stress.

In an embodiment, the drill is gripped in a holder so that its outer stepped portion axially extends a limited amount from the holder corresponding to the depth of the counterbore desired. Thus the holder forms a shoulder which constitutes a stop for drilling the channel with the counterbore into the tooth stub.

The aforementioned objects, features and advantages of the invention will, in part, be pointed out with particularity, and will, in part, become obvious from the following more detailed description of the invention, taken in conjunction with the accompanying drawing, which form an integral part thereof.

BRIEF DESCRIPTION OF THE DRAWINGS

FIG. 1 is an elevational view of the dental anchor, in accordance with the present invention;

FIG. 2 is an elevational view, partly in section, of the manipulating tool for insertion of the dental anchor of FIG. 1;

FIG. 3 is an elevational view, partly in cross-section, and on an enlarged scale of a drill for making the bores into a tooth stub body, and engaged in a drill holder;

FIG. 4 is a side view of the two-step drill for making the bores for the dental anchors according to the invention;

FIG. 8 is an elevational view, partly in cross-section, showing dental anchors of FIG. 1 in the final restored tooth.

DETAILED DESCRIPTION OF THE PREFERRED EMBODIMENTS

Figure 5:
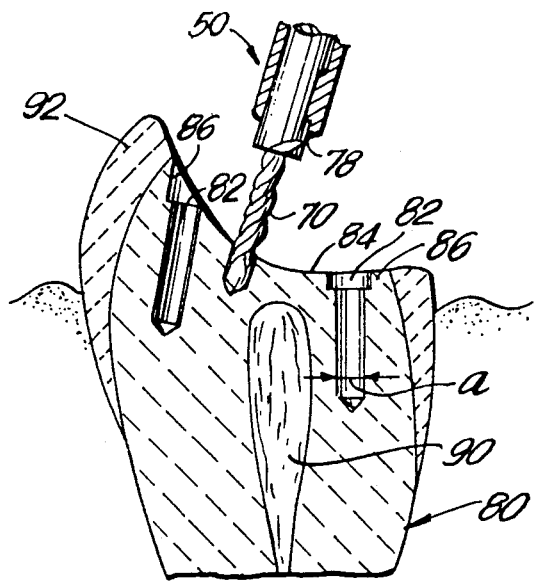
FIG. 5 is an elevational view, partly in cross-section, showing bores being formed in a tooth stub by means of a drill according to the invention.
Figure 6:
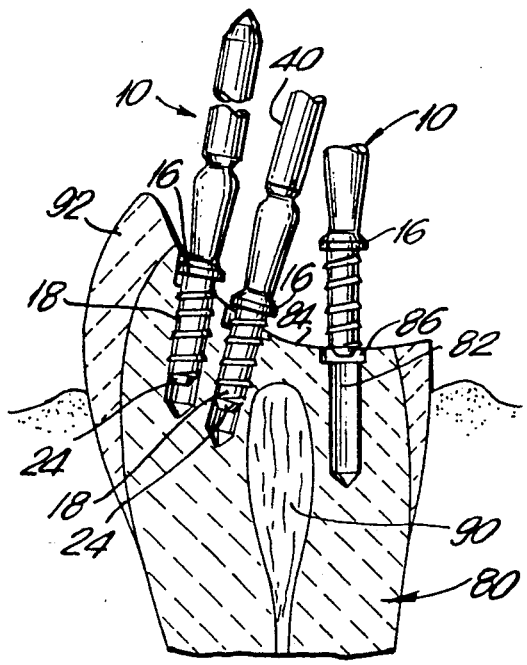
FIG. 6 is an elevational view, partly in cross-section, showing dental anchors of FIG. 1 being inserted into the bores found in FIG. 5.
Figure 7:
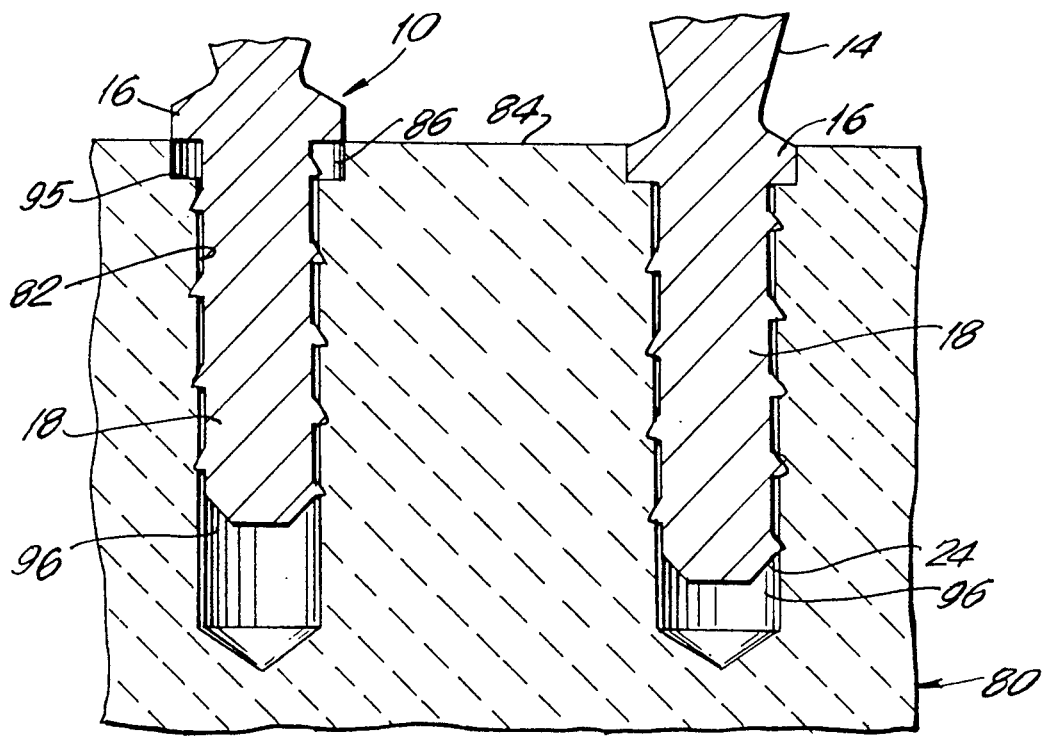
FIG. 7 is a sectional elevation view, on an enlarged scale, of the dental anchors, in partly and fully inserted conditions.

Referring now to the drawings in detail, FIG. 1 illustrates a dental anchor or pin 10 according to an embodiment of the present invention. Pin 10 includes an upper manipulating portion 12 which is typically held in a shank portion as shown in FIG. 2 and described hereinbelow, for insertion into a manual driver or an automatic drill. The pin 10 includes a retention portion 14, an intermediate stop member 16 and a lower anchoring portion 18. The latter is inserted in a channel or bore formed in the body of the tooth stub to anchor the pin into the tooth body. The stop member 16 is intended to limit the depth of insertion of pin 10 into the bore so that the retention portion 14 will extend upwardly from the exposed excavated surface of the tooth stub to form a retention means for a dental restoration formed on the tooth stub. The stop member 16 also serves to distribute stress, as will hereinafter be explained.

The anchoring portion 18 is formed as an elongated cylindrical body provided with a thread, shown as a helical reverse buttress-type thread 20 as is described in the aforementioned copending patent application. The buttress-type thread 20 has a substantially planar lower surface 22 which faces towards an insertion end 29 of the pin, and an angled or beveled upper surface 26 which tapers inwardly towards the retention portion 14 of pin 10. A knife-like cutting edge 28 is provided in the thread 20 between the planar surface. The threads on anchoring portion 18 are of a thread forming type which deform the dentin rather than cutting into the dentin. This also reduce stress on the tooth material as compared to thread-cutting pins.

The buttress-type thread utilized in the dental anchor according to this invention is disclosed in detail in the aforementioned assignee's co-pending patent application. The buttress-type thread is of a reverse construction where the beveled surface 26 tapers inwardly towards the upper end of pin 10. In such a reverse construction, the force required to pull pin 10 out from the bore formed in the tooth is increased as compared to dental anchors known in the dental art since, in addition to a vertical force required for pulling out the pin an additional force normal to the plane of the buttress thread angle is required to pull out the pin. This substantially enhances the retention of the anchoring portion of the pin within the bore of the tooth over threads of other types. Distal end 24 of the anchoring portion 18 is chamfered at 30 and tapers inwardly towards the end surface of the anchoring portion 18. Anchoring portion 18 is integral with the substantially cylindrical stop member or collar 16. The external diameter of the collar is greater than the largest diameter of the thread crest 28.

Retention portion 14 is an elongated barrel-like body having curved side walls tapering towards the collar 16 and merging at the upper end thereof into the substantially cylindrical manipulating portion 12. The angle $\alpha$ of tapering of the retention portion 14 downwards may vary between 5° and 10°. A transition zone or undercut 32 helps retain the restorative material in place. The elongated body of the retention portion 14 has no sharp corners or edges so that the whole retention portion of the pin 10, which receives thereon a dental restoration is extremely smooth. This significantly reduces stress in the restorative material thereby eliminating post curing (setting) cracks formed therein. Shaped undercut 32 permits packing of the restorative material to form a continuous band of restorative material under the upper part of the anchor to thereby help retain the dental restoration. The outer diameter of collar 16 is greater than the major diameter of the threads by approximately 10-15/1000".

Cylindrical manipulating portion 12 terminates at a substantially frusto-conical end portion 36 which has a conical proximal end 38. A reduced diameter neck 34 forms a fracture groove between the manipulating portion 12 and the retention portion 14 to facilitate shearing of the anchor from the manipulating portion. The elongated cylindrical surface of the manipulating portion 12 constitutes guide means for the insertion of pin 10 in a standard shank driver 40 shown in FIG. 2. Shank driver 40 is provided with a standard locking arrangement 42 for insertion into a dental handpiece. In the alternative, shank 40 can also be connected to a manual drive tool. Shank driver 40 is used to drive the pin 10 into a bore formed in the tooth stub body. An indent 44 can be provided on the manipulating portion 12 of pin 10 to wedge the pin in the shank driver 40. Any other suitable means for firmly retaining pin 10 in the shank driver 40 can be also used to allow pin 10 to be rotated and inserted in a corresponding bore in the tooth stub body. Pins 10 may be made of stainless steel, titanium or any other suitable material.

FIGS. 3 and 4, illustrate a spiral drill 50 for producing bores or channels in the tooth body receiving the anchors previously described. Drill 50 is inserted in a shank driver 52 having an elongated cylindrical body provided at its proximate end with a standard coupling arrangement 54 for insertion into a dental handpiece. Drill 50 includes a substantially cylindrical guide portion 56 insertable and fixable in a cylindrical blind hole 58 formed in a drill receiving portion 60 of a reduced diameter front end 61 of the shank driver 52. The external cylindrical surface of the drill receiving portion 60 slightly tapers at 78 towards the distal end of the drill holder.

As best shown in FIG. 4, a recess 62 formed in the upper surface of the guide portion 56 of the drill bit 10 extends in the direction of the axis of the drill. An inwardly protruding elongated portion 64 formed on the inner surface limiting the blind hole 58 is snapped or keyed in recess 62 to firmly grip drill 50 in the shank driver 52. Two coaxial stepped drilling portions or bits 70 and 72 of different diameters are provided in drill 50. Drill bit 72 of a greater diameter than that of drill bit portion 70 is provided to produce a counterbore at the mouth of the main bore formed by the drill portion 70, as will be explained below.

As shown in FIG. 3 guide portion 56 of the drill 50 is dimensioned so that it extends outwardly from the shank driver 52 to produce a protruding portion 76 of the larger diameter drill portion 72. The edge 78 of the shank forms a stop shoulder. This shoulder constitutes a stop for drilling and ensures a fixed length of the bore and a fixed depth of the counterbore. Holder portion 60 has its distal end curved at 78 to avoid sharp corners and prevent a striking effect on the exposed excavated surface of the tooth stub during the drilling process.

The ratio between the length of the larger stepped drilling portion 72 and that of the main thinner drilling portion 70 amounts to 1:4 to 1:5 and, with drills 0.300 in. long the length of portion 72 is between 0.015 and 0.20 in.

Referring now to FIGS. 5 to 8, it is seen that the tooth to be prepared typically includes a dentin material 80, a pulp channel 90 and a layer of enamel 92. The stepped spiral drill 50 is urged into the dentin material of the tooth 80 to produce a plurality of channels and bores 82 extending into dentin 80 from an exposed excavated surface 84 from which decay was removed before drilling channels 82. The number of bores 82 varies with the area of exposed excavated surface 84 and the size of a dental restoration further to be built on the tooth. The diameter of the drill bit may be of a size depending on the pin size and tooth area. In one embodiment a diameter of 0.028 inches was used. As bore 82 is drilled by bit portion 70, the drill is further inserted into this bore until the enlarged drill bit portion 72 enters the dentin material at the proximal end or mouth of bore 82 and forms a counterbore 86.

As mentioned hereinabove shoulder 78 formed by the drill shank driver 52 limits the insertion of the enlarged portion 72 of the drill into the dentin material and thus the depth of the counterbore 86 substantially to the height of the collar 16 of the pin 10 which is to be received in the respective bore. After a desired number of bores 82 with counterbores 86 have been produced, anchoring pins 10 are inserted into each of bores 82. It will be apparent that the diameter of the anchoring portions 18 of each pin is greater than the diameter "a" of the bore 82. Thus the anchoring portion 18 of each pin is tightly threaded into its respective bore 82 as the shank driver 40 which holds the manipulating portion 12 of the pin is rotated. As pin 10 is urged further into bore 82 collar 16 of pin 10 enters the counterbore 86 and seats in the counterbore thus limiting any further extension of the pin end 24 into the distal blind end 96 of the bore. The counterbore 86 may extend by 1/1000 to 15/1000" below the surface 84 of the tooth. Upon insertion the pins shear at their reduced diameter portions and remain in place in the tooth stub.

In conventional anchoring pins, the pins are introduced into respective bores formed in the tooth stub. The blind end of each bore has a mating angled configuration similar to the distal end of the anchoring portion of the pin and forms a seat therefor. As the pin is inserted, it continues till the pin bottoms out at the bottom of the bore where stress is exerted on the body of the tooth. The stress is concentrated. Such stress not only exists at the time of insertion but even during loading.

In the present pin because collar 16 seats in the counterbore 86, it prevents the pin from bottoming out. This eliminates the stress at the lower end of the bore. Furthermore the collar distributes the stress over a much greater surface area than that of the distal end 24 of the pin. In addition, because the collar has a diameter greater than the crest of the threads, the collar sits on solid dentition that is not over a threaded undermined, edge, as shown at 95 in FIG. 7. Thus the stress is distributed in the region supported by solid dentition rather than in the region of the thread. The sizing of the drill with the mating size of the anchor is such that when the collar 16 is received in counterbore 86 a clearance of at least about one fourth of a mm remains between distal end 24 of the pin and the blind end 96. The collar and counterbore combination according to the present invention not only re-distributes stress on the tooth during the insertion of the pin but also significantly reduces stress during loading of the tooth. Collar 16 will constitute a positive stop preventing the threads from crushing. As the lower surface of collar 16 reaches the bottom of counterbore 86, shank holder 40 shears off at the reduced diameter section to enable pin 10 to be anchored in the bore.

It will be also appreciated that due to the fact that the retention portion of pin 10 has no sharp corners and is anatomically shaped, stresses in the upper restorative material would also be reduced and post setting cracks in the amalgam or composite would be substantially prevent from the occurrence.

It should be also noted that at inclined portions of the excavated surface 84 the counterbore 86 produced in the tooth body 80 may be incomplete due to the tooth's anatomy as illustrated at the left-hand channel 82 of FIG. 5. However, by making even a part of the counterbore, a flat bottom surface is produced on which the collar can sit. Thus, even though the tooth surface is uneven or inclined, nevertheless the pin will sit along a flat even surface of the counterbore and distribute the stress. Also, the collar 16 will sit within such counterbore and still, limit the further insertion of the pin into the bore.

FIG. 8 shows a completed restoration with three pins 10 being employed and with the restorative material of choice 100 being secured over the pins. If necessary, a final outer cap 102 can be secured to the core. It should be appreciated that in some cases, a post could also be used with one or two of the pins and positioned in the tooth stub.

It should be understood, of course, that the foregoing disclosure relates to only a preferred embodiment of the invention and that it is intended to cover all changes and modifications of the example of the invention herein chosen for the purpose of the disclosure, which modifications do not constitute departures from the spirit and scope of the invention.

What is claimed is:

1. A dental anchor for use in the retention of a superstructure on a tooth stub and insertable into a blind bore formed in the tooth stub, comprising:
   an upper retention portion to form retention means for the superstructure formed on the tooth stub;
   a lower anchoring portion formed in one-piece with said retention portion and having anchoring means thereon to anchor said dental anchor in the tooth stub,
   said anchoring means including a thread for self-threading engagement of said anchoring portion in said bore; and
   stop means interconnected between said retention portion and said anchoring portion and limiting depth of insertion of said anchoring portion into said bore,
   said retention portion being of smooth configuration, having a non-interrupted external surface and being formed without any sharp corners to thereby substantially minimize stress on the superstructure on said retention portion.

2. Dental anchor of claim 1, wherein shaped undercuts are formed between said stop means and said retention portion.

3. Dental anchor of claim 1, further including a manipulating portion axially extending upwardly from and connected to said retention portion, said manipulating portion being separable from said retention portion after said anchoring portion has been self-threaded in said channel.

4. Dental anchor of claim 3, further including a reduced diameter portion interconnected between said retention portion and said manipulating portion to facilitate separation of said manipulating portion from said retention portion.

5. A dental anchor for use in the retention of a superstructure on a tooth stub and insertable into a blind bore formed in the tooth stub, comprising:
   an upper retention portion to form retention means for the superstructure formed on the tooth stub;
   a lower anchoring portion having anchoring means thereon to anchor said dental anchor in the tooth stub,
   said anchoring means including a thread for self-threading engagement of said anchoring portion in said bore; and
   stop means interconnected between said retention portion and said anchoring portion and limiting depth of insertion of said anchoring portion into said bore,
   said retention portion being of smooth configuration, having a non-interrupted external surface and being formed without any sharp corners to thereby substantially minimize stress on the superstructure retained on said retention portion, wherein said retention portion is elongated and has a barrel-shaped configuration tapering towards said anchoring portion.

6. Dental anchor of claim 5, wherein said retention portion converges towards said stop means.

7. A dental anchor for use in the retention of a superstructure on a tooth stub and insertable into a blind bore formed in the tooth stub, comprising:
   an upper retention portion to form retention means for the superstructure formed on the tooth stub;
   a lower anchoring portion having anchoring means thereon to anchor said dental anchor in the tooth stub,
   said anchoring means including a thread for self-threading engagement of said anchoring portion in said bore; and
   stop means interconnected between said retention portion and said anchoring portion and limiting depth of insertion of said anchoring portion into said bore,
   said retention portion being of smooth configuration, having a non-interrupted external surface and being formed without any sharp corners to thereby substantially minimize stress on the superstructure retained on said retention portion, wherein said stop means includes a substantially cylindrical collar.

8. Dental anchor of claim 7, wherein an outer diameter of said collar is greater than that of a crest of said thread.

9. A dental anchor for use in the retention of a superstructure on a tooth stub and insertable into a blind bore formed in the tooth stub, comprising:
   an upper retention portion to form retention means for the superstructure formed on the tooth stub;
   a lower anchoring portion having anchoring means thereon to anchor said dental anchor in the tooth stub,
   said anchoring means including a thread for self-threading engagement of said anchoring portion in said bore; and
   stop means interconnected between said retention portion and said anchoring portion and limiting depth of insertion of said anchoring portion into said bore,
   said retention portion being of smooth configuration, having a non-interrupted external surface and being formed without any sharp corners to thereby substantially minimize stress on the superstructure retained on said retention portion, wherein said thread is a helical buttress-type thread.

10. Dental pin of claim 9, wherein said buttress-type thread has a substantially lower surface facing towards a distal insertion of said anchoring portion, an angled upper surface tapering inwardly towards said upper retention portion, and a sharp edge disposed between said planar lower surface and said angled upper surface.

11. In combination, a dental anchor for insertion within a bore formed in a tooth stub, for retention of a superstructure on a tooth stub, and a dental drill for drilling the bore to receive the dental anchor, the anchor comprising:
   an elongated pin including an anchoring portion formed with a thread for self-threading engagement in said bore, a retention portion having a smooth configuration for retaining the superstructure thereon, and a cylindrical non-tapered stop portion,
   interconnected between said retention portion and said anchoring portion,
   said drill comprising a substantially elongated first drill bit for producing said bore and an integral, coaxial second drill bit of a diameter greater than that of said first drill bit for producing at the mouth of said bore at an exposed excavated surface of said tooth stub a countersink for receiving said stop portion of said pin, whereby stress exerted on said tooth with said pin inserted therein is distributed over a non-threaded surface of the tooth.

12. The combination of claim 11, wherein said stop portion is a cylindrical collar, said drill being stepped with one step section forming said first drill bit and another step section provided over a portion thereof with said second drill bit.

13. The combination claim 12, further including a shank holder engaging said another step section so that said first and second drill bits extends axially outwardly therefrom to thereby produce on said shank holder a shoulder limiting depth of drilling of said bore with said counterbore, wherein the length of said first and second drill bits extending from said shoulder are sized to produce a bore and counterbore less than the length of said anchoring portion and collar to cause the collar to stop at the counterbore before the anchoring portion bottoms out at a bottom of the bore.

14. The combination of claim 13, further including means for retaining said drill in said shank holder.

15. A dental drill for producing a bore in a tooth stub to accommodate therein a dental anchor for retention of a superstructure on the tooth stub, said dental drill comprising:
a substantially cylindrical stepped body including a first step portion provided with a first drill bit for drilling an elongated bore in the tooth stub, and a second step portion coaxial with said first step portion and being of a diameter greater than that of said first step portion and having over a part thereof a second drill bit shaped for contouring at the mount of said bore at an exposed excavated surface of the tooth stub a cylindrical non-tapered countersink open at said surface of a fixed depth; retention means for securing the second step portion during rotation, said retention means including a sleeve portion receiving said second step portion so that said second drill bit protrudes outwardly therefrom; and shoulder means on said sleeve portion for limiting the depth of the bore and counterbore formed into the tooth stub.

16. A dental drill of claim 15, wherein the ratio between the length of said second drill bit and the length of said first drill bit is in the range of 1:10 to 1:8.

17. A method of preparing a tooth stub for building a superstructure thereon, comprising the steps of:
preparing an exposed excavated surface of the tooth stub;
providing a stepped dental drill including a fist drill bit, and a second drill bit of a diameter greater than that of said first drill bit and of a substantially smaller length than that of said first drill bit;
providing a drill shank holder and firmly engaging said drill in said holder so that said first and second drill bits extend axially outwardly from said shank holder and form with an end of said holder a limiting shoulder;
a drilling in said tooth at least one bore by urging said first drill bit into the tooth;
contouring a cylindrical countersink in said bore at said exposed excavated surface by continued drilling thereby urging said second drill bit into the tooth until said limiting shoulder reaches exposed excavated surface;
providing at least one elongated dental anchor including an upper manipulating portion, an intermediate retention portion of a smooth configuration and connected to said manipulating portion at a transition zone of a reduced diameter, a cylindrical stop connected to said retention portion, and an anchoring portion having a thread thereon and connected to said stop;
providing a retaining holder for said dental anchor;
engaging said manipulating portion of said anchor in said retaining holder;
inserting said anchoring portion into said bore by rotating said retaining holder to cause self-threading engagement of said anchoring portion in said bore;
further rotating said retaining holder with said anchor engaged therein until said cylindrical stop is situated in said countersink and a further insertion of said anchor into said bore is prevented, the distal end of said anchoring portion being spaced from the bottom end of the bore, whereby said retention portion and said manipulating portion extend upwardly from said exposed excavated surface of the tooth; and
severing said manipulating portion from said retention portion at said transition zone by said retaining holder.

18. A dental anchor for use in the retention of a superstructure on a tooth stub and insertable into a blind bore formed in the tooth stub, comprising:
an upper retention portion to form retention means for the superstructure formed on the tooth stub;
a lower anchoring portion having anchoring means thereon to anchor said dental anchor in the tooth stub,
said anchoring means including a thread for self-threading engagement of said anchoring portion in said bore; and
stop means interconnected between said retention portion and said anchoring portion and limiting depth of insertion of said anchoring portion into said bore,
said retention portion being of smooth configuration without any sharp corners to thereby substantially minimize stress on the superstructure retained on said retention portion,
wherein said stop means includes a substantially cylindrical collar.

19. Dental anchor of claim 18, wherein shaped undercuts are formed between said collar and said retention portion.

20. Dental anchor of claim 18, wherein said retention portion is elongated and has a barrel-shaped configuration tapering towards said anchoring portion.

21. Dental anchor of claim 18, further including a manipulating portion axially extending upwardly from and connected to said retention portion, said manipulating portion being separable from said retention portion after said anchoring portion has been self-threaded in said bore.

22. Dental anchor of claim 21, further including a reduced diameter portion interconnected between said retention portion and said manipulating portion to facilitate separation of said manipulating portion from said retention portion.

23. Dental anchor of claim 18, wherein said retention portion converges towards said collar.

24. Dental anchor of claim 18, wherein an outer diameter of said collar is greater than that of a crest of said thread.

25. Dental anchor of claim 18, wherein said thread is a helical reverse buttress-type thread.

26. Dental pin of claim 26, wherein said buttress-type thread has a substantially lower surface facing towards a distal insertion of said anchoring portion, an angled upper surface tapering inwardly toward said upper retention portion, and a sharp edge disposed between said planar lower surface and said angled upper surface.

* * * * *